United States Patent [19]

Lyman et al.

[11] Patent Number: 5,466,602
[45] Date of Patent: * Nov. 14, 1995

[54] APPARATUS FOR GROWING TISSUE CULTURES IN VITRO

[75] Inventors: George Lyman, Cape Porpoise, Me.; Gregory Mathus, Concord; David Root, Lexington, both of Mass.

[73] Assignee: Data Packaging Corporation, Cambridge, Mass.

[*] Notice: The portion of the term of this patent subsequent to Jun. 25, 2008, has been disclaimed.

[21] Appl. No.: 180,695

[22] Filed: Jan. 13, 1994

Related U.S. Application Data

[63] Continuation of Ser. No. 835,136, Mar. 18, 1992, abandoned, which is a continuation of Ser. No. 695,300, May 3, 1991, Pat. No. 5,215,920, which is a continuation of Ser. No. 841,562, Mar. 20, 1986, Pat. No. 5,026,649.

[51] Int. Cl.$^6$ .................................................. C12M 3/06
[52] U.S. Cl. ................................ 435/297.1; 435/289.1
[58] Field of Search ............................... 435/284–286, 435/296–301, 310, 311; 422/101, 102; 210/321.84

[56] References Cited

U.S. PATENT DOCUMENTS

| 2,677,646 | 5/1954 | Lovell et al. | 435/297 X |
|---|---|---|---|
| 2,761,813 | 9/1956 | Goetz | 435/301 X |
| 3,275,528 | 9/1966 | Ainis | 435/284 |
| 3,540,856 | 11/1970 | Rochte et al. | 422/101 |
| 4,012,288 | 3/1977 | Lyman et al. | 435/298 X |
| 4,125,436 | 11/1978 | Liner | 435/287 |
| 4,246,339 | 1/1981 | Gole et al. | 422/102 X |
| 4,308,351 | 12/1981 | Leighton et al. | 435/284 |
| 4,349,632 | 9/1982 | Lyman et al. | 435/284 |
| 4,603,105 | 7/1986 | Kaplan | 435/297 X |
| 4,608,342 | 8/1986 | Nees | 435/297 X |
| 4,670,396 | 6/1987 | Bear et al. | 435/310 X |
| 4,686,190 | 8/1987 | Cramer et al. | 435/285 X |
| 5,026,649 | 6/1991 | Lyman et al. | 422/101 |
| 5,215,920 | 6/1993 | Lyman et al. | 435/284 |

FOREIGN PATENT DOCUMENTS

| 1572527 | 6/1969 | France . | |
|---|---|---|---|
| 2563232 | 4/1984 | France | 435/298 |
| 839245 | 4/1952 | Germany . | |
| 1003489 | 2/1957 | Germany . | |
| 3317550 | 5/1983 | Germany . | |

OTHER PUBLICATIONS

McCall et al. "The Culture of Vascular Endothelial Cells to Confluence on Microporous Membranes." Thrombosis Research. (vol. 24)(1981) pp. 417–431.

Shasby et al., Blood, vol. 65, No. 3 (Mar.), 1985, pp. 605–614.

Hennig et al., Arteriosclerosis, vol. 4, No. 5, Sep./Oct. 1984, pp. 489–497.

Grobstein. "Trans–Filter Induction of Tubules in Mouse Metanephrogenic Mesenchyme", Experimental Cell Research, vol. 10 (1956) pp. 424–440.

Primary Examiner—William H. Beisner
Attorney, Agent, or Firm—Wolf, Greenfield & Sacks

[57] ABSTRACT

The present invention relates to an apparatus for growing tissue culture in vitro. The apparatus features a housing which fits into a well containing media. A bottom membrane surface is maintained at a depth within the well, and the housing centered in the well by a flange and rim which cooperate with the well.

3 Claims, 3 Drawing Sheets

APPARATUS FOR GROWING TISSUE CULTURES IN VITRO

This application is a continuation of application Ser. No. 07/835,136 filed Mar. 18, 1992, now abandoned, which is a continuation of application Ser. No. 07/695,300 filed May 3, 1991, now U.S. Pat. No. 5,215,920 issued Jun. 1, 1993, which is a continuation of application Ser. No. 06/841,562 filed Mar. 20, 1986, now U.S. Pat. No. 5,026,649 issued Jun. 25, 1991.

INTRODUCTION

This invention relates to apparatus for growing tissue cultures in vitro and more particularly comprises a new and improved device for supporting tissue cultures in a fluid medium containing nutrients which promote the tissue culture growth. Until quite recently, in the conventional art of in vitro growth of mammalian tissues, tissue samples were affixed to the bottom of a tube or petri dish and bathed from above with a nutrient solution. In that mode, the tissue culture receives nutrients from above, i.e., from the side opposite the side .attached to the tube or petri dish. That arrangement is contrary to the situation in the body where the plane of attachment of epithelial tissue to the underlying connective tissue is also the path of nutrient exchange. That prior art technique made the diagnosis and prediction of the malignant character of many epithelial tissue disorders very difficult.

More recently, perhaps dating from the publications of Dr. Joseph Leighton and the issuance of the Leighton et al. U.S. Pat. No. 4,308,351 dated Dec. 29, 1981 wherein many of his publications are listed, tissue cultures have been grown in vitro while receiving substantial quantities of nutrients for growth through a permeable membrane to which the tissue culture is attached. One widely used device is in the form of a molded plastic sleeve having a membrane secured across one end and on which the tissue culture is affixed within the sleeve. The sleeve has projecting feet at the end to which the membrane is attached, which serve to support the membrane-sleeve assembly in the well of a culture cluster dish. That device has several disadvantages. For example, the sleeve-membrane assembly is free to float in the fluid in the well, and therefore, the sleeve can move to a position closely adjacent the wall at one point about its diameter so as to permit capillary action which will cause the fluid outside the sleeve to wick up the sleeve and pass either into the sleeve or out of the well. Furthermore, the feet on the end of the sleeve to which the membrane is attached make it somewhat difficult to assemble the membrane on the sleeve. Yet another disadvantage of the prior art device is that it has no means by which the sleeve can be supported in an increased depth of nutrient solution in the well below the membrane. Rather, that depth is always limited to the height of the feet.

One important object of the present invention is to provide a membrane support which precisely positions the membrane-support assembly coaxially within the tissue culture cluster dish well in which it is mounted.

Another object of the present invention is to provide a support for membrane on which tissue culture is grown in vitro, which will prohibit capillary action between it and the container for the fluid medium in which the membrane-support assembly is placed.

Yet another object of the present invention is to provide a membrane-support assembly which allows a pipette to be inserted between the support and cluster dish well in which it is placed without disturbing or removing the assembly so that fluid may be introduced to or removed from the space between the support and well and beneath the membrane.

Yet another object of the present invention is to provide a membrane-support assembly which will so position the culture cluster dish lid so as to achieve a controlled evaporation rate for the fluid in the wells of the dish.

To accomplish these and other objects, the present invention includes a flat permeable membrane which is attached to one end of an essentially tubular support. The other end of the tubular support includes an outwardly extending flange which in turn carries a rim that can hang upon the upper end of a well in a tissue culture cluster dish. The flange centers the support in the well and prevents it from shifting laterally in the well. Therefore, the circular generally cylindrical wall of the support will not move close to the inner surface of the well wall in which it is placed so as to cause capillary action of the fluid in the well. The generally cylindrical side wall of the support is provided with a number of openings which allow a pipette to be inserted into the space between the support and well wall so that the pipette may reach the bottom of the well and introduce or remove medium from beneath the membrane and about the sides of the support. Knobs are provided on the upper surface of the rim which are adapted to engage the top wall of the lid of the tissue culture cluster dish so as to provide communication between the atmosphere and the interior of the support to control the evaporation rate of the fluid.

The membrane-support assembly is sized to be used with a cluster dish having wells of a specific size so as to provide the proper clearance about the support and engage the top end of the well. The membrane-support assembly may be made in different sizes so as to be used with different sizes of cluster dishes.

These and other objects and features of the present invention will be better understood and appreciated from the following detailed description of one embodiment thereof, selected for purposes of illustration and shown in the accompanying drawings.

BRIEF FIGURE DESCRIPTION

DETAILED DESCRIPTION

Figure 1:
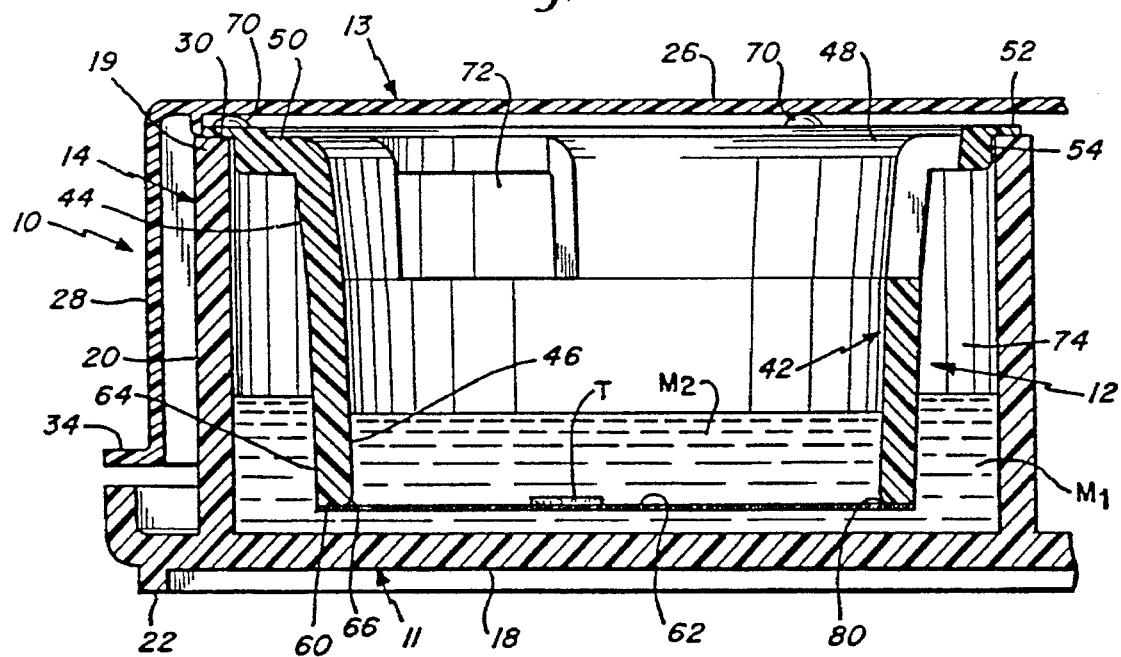
FIG. 1 is a cross-sectional view through one well of a tissue culture cluster dish and a membrane-support assembly constructed in accordance with the present invention and showing a tissue sample on the membrane.

The apparatus for growing tissue cultures in vitro shown in FIGS. 1 and 2 includes a tissue culture cluster dish 10 and a membrane-support assembly 12 which are described in detail below.

The tissue culture dish 10 is only partially illustrated in the drawings but is shown in detail in U.S. Pat. No. 4,495, 289 dated Jan. 2, 1985 and assigned to Data Packaging Corporation, the assignee of the present invention. In the present application, only one well 14 of the cluster dish is shown, and it is to be appreciated that the cluster dish may have six, twelve, twenty-four or some other number of wells selected for the particular purpose for which the apparatus is used. Of course, each of the wells of the dish may contain a separate membrane-support assembly. As each of the other wells is identical to the well shown and each is used independently of the other, but a single well is illustrated.

The cluster dish 10 has a base 11 and lid 13. The base has a number of wells 14 each closed at the bottom by wall 18 and open at the top end 19. The side wall 20 of each well 14 is generally cylindrical and may include a slight draft which facilitates removal of the base from the mold in which it is formed. The base also includes a downwardly extending peripheral rib 22 on the lower side of its bottom wall 18 that supports the base on any working surface on which it is placed with the bottom wall 18 elevated above the working surface. The base 10 typically is transparent and may be molded of polyvinylchloride.

Lid 13 which may be molded of the same material as the base 10 has a top wall 26 and a surrounding depending skirt 28. When positioned on the base without anything projecting upwardly from the wells, the lid top wall 26 is spaced above the top edges 30 of the wells so as not to seal the open top ends 19 of the wells. The lid may be supported in that position by protrusions (not shown) on the base which engage the lower flange 34 of the lid skirt 28.

While in the foregoing paragraphs, the details of the cluster dish illustrated are described, it is to be appreciated that the details of the dish do not from part of the present invention, and the permeable membrane and its support may be sized to fit and be used with other cluster dishes.

The membrane-support assembly 12 of this invention includes an essentially tubular support 42 having an upper portion 44 and lower portion 46. The upper portion 44 is open at the top 48 and carries an outwardly extending flange 50 which serves to position the support in the well 14 of the culture dish.

Flange 50 carries a rim 52 that extends radially outwardly from the upper edge of the flange. The flange and rim together form a shoulder 54 that precisely positions the support 42 in well 14. The outer diameter of shoulder 54 is very slightly less than the inner diameter of the cylindrical wall 20 of well 14 at the top while the rim 52 exceeds the inner diameter of the inner surface of wall 20 and therefore rests upon the top edge 30 of the wall when the support is positioned in the well. This arrangement is clearly shown in FIGS. 1 and 2. With the support 42 in the position shown, it is evident that the support has little or no freedom to move laterally in the well 14. Similarly, the rim 52 prevents the support 42 from dropping to the bottom wall 18 of the well.

The lower portion 46 of the support has a flat bottom end 60 to which the membrane 62 of the assembly is attached. Typically, the membrane 62 is attached to the end 60 by either heat sealing or solvent bonding the two together. The periphery of the membrane 62 is trimmed flush with the outer surface 64 of the lower portion 46 of the support. It will be noted in FIG. 5 that a radius 66 is provided at the inner edge of bottom end 60 so as to prevent tearing of the membrane when the support and membrane are secured together. The membrane may be made of any suitable material including perforated inert film, hydrated gel or a layered combination wherein the latter is supported by the former.

Figure 5:
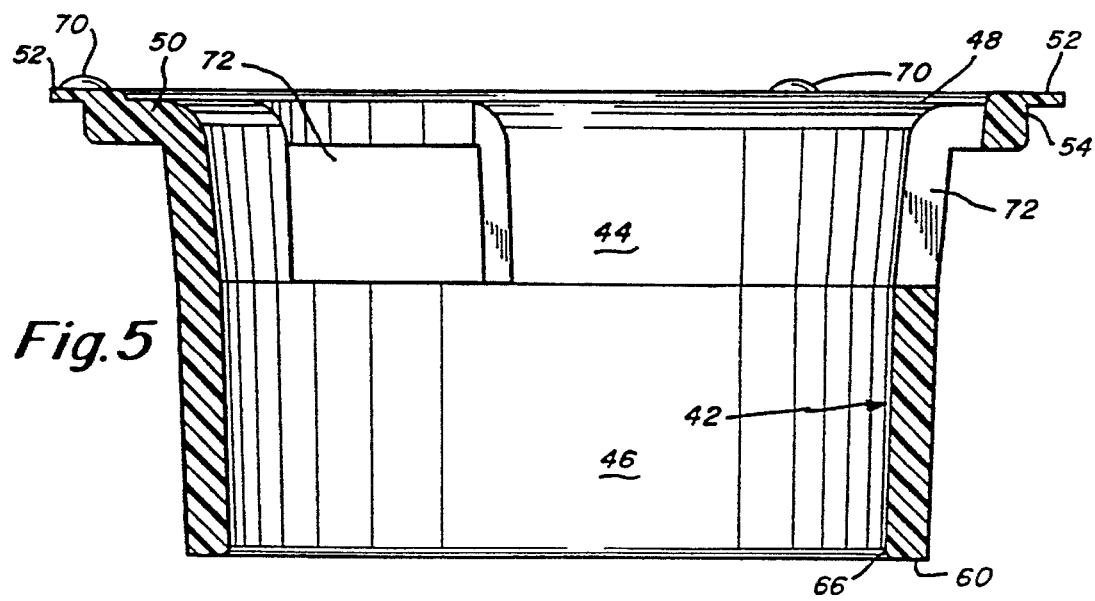
FIG. 5 is a cross-sectional view of the support taken along section line 5—5 in FIG. 3.

It will also be noted in FIG. 5 that the lower portion 46 of the support is provided with a slight draft, typically 2°, to facilitate the molding of the support. The upper portion 44 of the support is provided with a greater draft (6° is suggested). This 6° draft also assists in the molding operation by reducing the mold wear.

Figure 3:
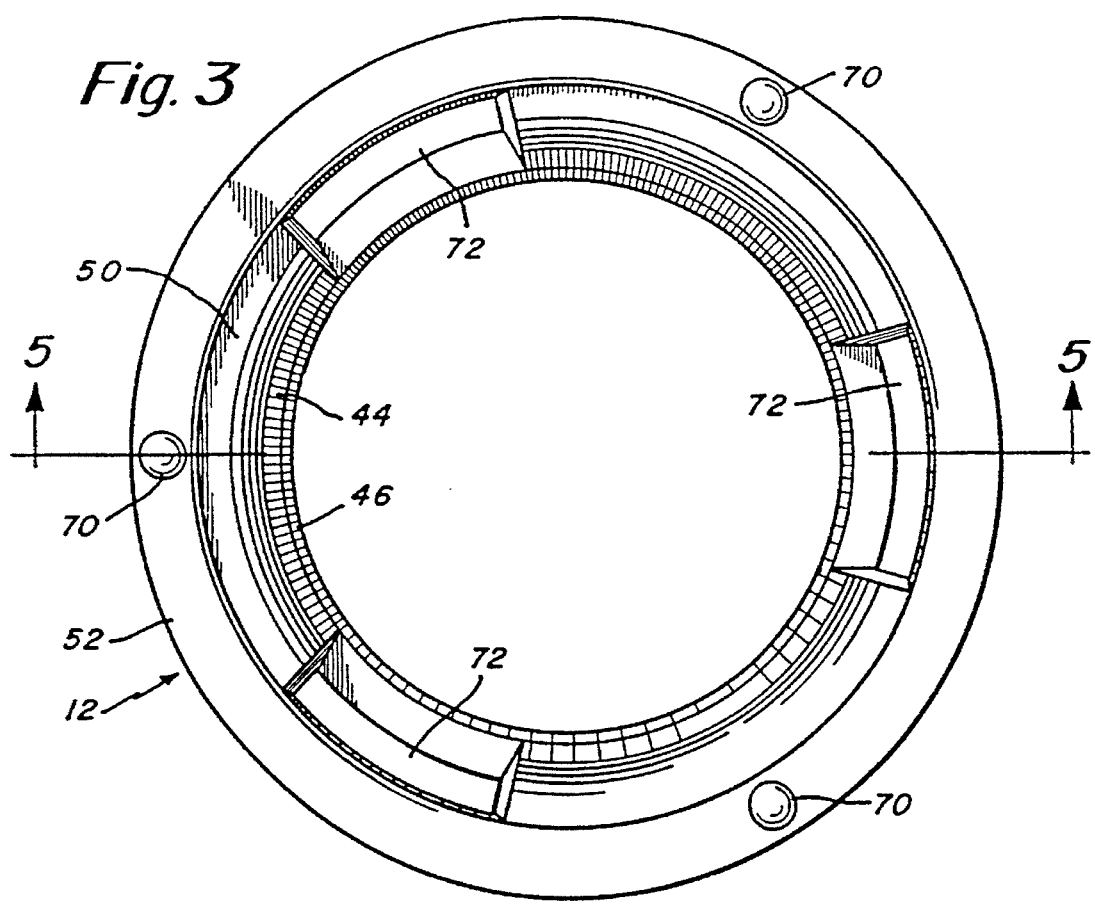
FIG. 3 is a plan view of the membrane support shown in FIGS. 1 and 2.
Figure 4:
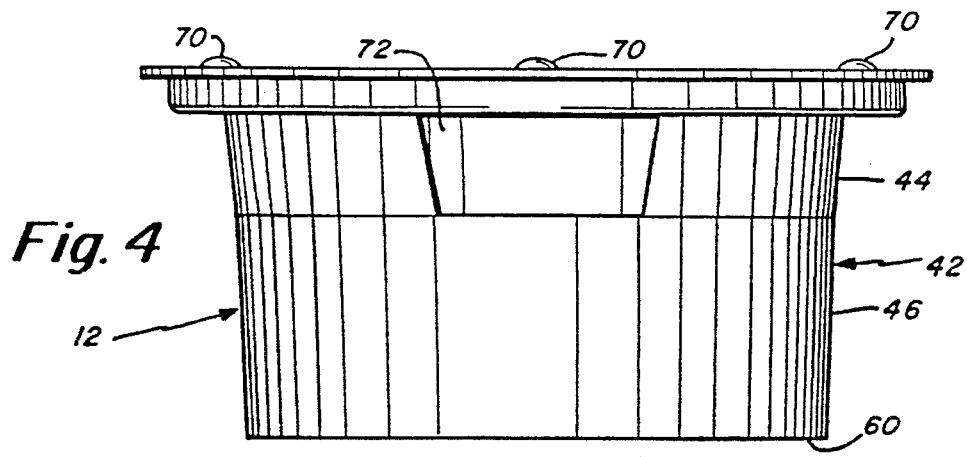
FIG. 4 is a side view of the support.

The rim 52 on flange 50 of support 42 carries a plurality of spaced knobs 70 that are intended to engage the bottom surface of top wall 26 of lid 13 of the cluster dish 10 so as to provide communication between the interior of well 14 (within and without membrane-support assembly 12) and the atmosphere. The spaced knobs 70, three of which are shown in FIG. 3, provide a controlled evaporation rate of the fluid in the well.

Three relatively large openings 72 are formed in the upper portion 44 of the support 12 spaced equidistantly about its circumference. The openings 72 extend into the flange 50. The function of the openings 72 is illustrated in FIG. 2 wherein a pipette tip 75 is shown to extend through one opening 72 to a position immediately adjacent the bottom wall 18 of the well 14. Thus, the openings 72 provide access to the annular space 74 between support 42 and well wall 20 and to the region below the membrane 62 so that medium may be introduced to or removed from those locations without disturbing or in any way removing the support from the well. The membrane-support assembly, however, can be lifted from the well 14 at any time merely by removing the lid 13.

In FIG. 1 a tissue culture sample T is shown secured to the upper surface of the membrane 62. A nutrient solution $M_1$ is shown to partially fill the annular space 74 in well 14 and the space below the membrane 62 that comprises a second compartment. Depending upon the particular test or experiment being conducted, the same or a different solution $M_2$ may be disposed within the support 42 and in contact with the tissue sample T and the upper surface of the membrane 62. The fill height of the separate solutions $M_1$ and $M_2$ in the annular space 74 and within the support 42 (the separate compartments) may or may not be the same.

Figure 2:
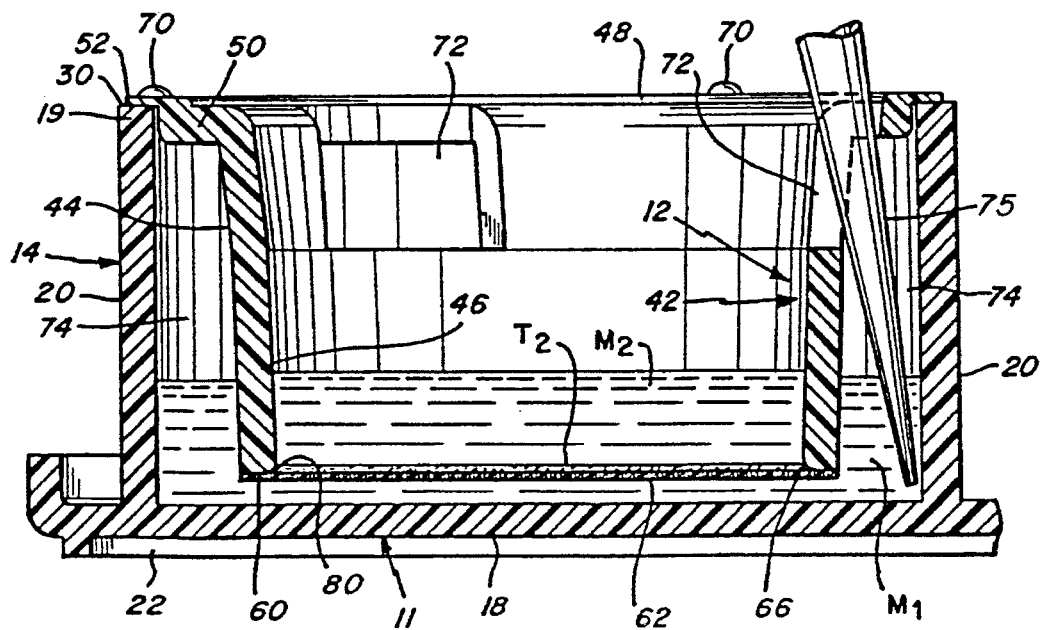
FIG. 2 is a cross-sectional view similar to FIG. 1 with the lid removed from the tissue culture cluster dish and showing how a pipette may be inserted into the space between the support and the well so as to add or remove fluid and further showing the tissue culture grown so as to cover the membrane.

In order to promote the growth of a monolayer of cells on the upper surface of the membrane within the support 42 as suggested in FIG. 2, the support 42 and the membrane may be treated by corona discharge or other technique so as to reduce surface tension of the surfaces. When so treated the tissue sample T and the tissue culture cultivated in the system will attach firmly to the membrane and seal at the edges 80 of the membrane 62 where the membrane joins the radius 66 of lower end 60 of the support. In FIG. 2, a thin monolayer of tissue cells $T_2$ is suggested extending to the edges of the membrane.

During the growth of the tissue culture, the lid 26 of the culture plate is placed over the base as suggested in FIG. 1, and when desired the lid may be removed and a pipette inserted as shown in FIG. 2 to either remove or add medium to the space 74. The tissue culture will receive a substantial portion of its nutrients required for growth through the permeable membrane 62. Thus, a very simple system is provided which achieves the several objects of the invention set forth above.

It will be appreciated that because the support 42 is set within the well 14 and spaced sufficiently from the well side wall 20, no capillary action will occur to cause the solution in the space 74 from wicking up the wall and entering the interior of the support through the openings 72 or spilling from the well 14. When the membrane-support assembly is positioned in the well, the lid 13 serves to hold the assembly in position within the well. Consequently, the assembly cannot float in the solution and cause the rim 52 to unseat. Furthermore, because the flange and rim 50 and 52 support the membrane-support assembly, the culture may be treated if desired in a deeper well than suggested so as to provide more solution beneath the membrane. While it is customary to position the membrane 62 approximately 1 mm above the bottom wall 18, if desired, a well of greater depth may be used so as to provide additional space between the member and the bottom wall 18.

It will be appreciated that the tissue sample T attached to the membrane receives nutrients by diffusion through the membrane 62 from the nutrient bath provided in the well 14. Additional nutrients may be received from the solution within the well.

Having described this invention in detail, those skilled in the art will appreciate that numerous modifications may be made thereof without departing from its spirit. Therefore, it is not intended to limit the breadth of this present invention to the single embodiment illustrated and described. Rather, the scope of this invention is to be determined by the appended claims and their equivalents.

What is claimed is:

1. A device for growing cells or tissues for use with a well having a well housing having at least one side wall and a well bottom defining a well chamber for receiving media, comprising:

a housing having a wall, a top end, a bottom end, and a flange, said bottom end having a permeable membrane, said permeable membrane having a top surface and a bottom surface, said top surface for receiving one or more cells for culture, and said bottom surface for positioning in a juxtaposed spaced relationship to said well bottom to allow said cells to receive media held in said well through said permeable membrane, said wall capable of being received within said well chamber, in spaced relationship with said side walls of said well to define an annular space which annular space does not allow capillary action with aqueous fluid, and said flange extending radially from the top end of said wall and capable of being received on said well housing to suspend said wall within said well chamber, said flange having a rim capable of being received by said side wall to preclude lateral movement of said housing in said well chamber for positioning said wall in said well chamber to maintain said annular space, and said spaced relationship between said well bottom and said bottom surface of said permeable membrane.

2. The device as claimed in claim 1 wherein said flange extends along the entire periphery of said wall.

3. The device as claimed in claim 1, further comprising tissue or cell growth on said permeable membrane.

* * * * *